(12) United States Patent
Sonderegger (10) Patent No.: US 11,547,795 B2
(45) Date of Patent: Jan. 10, 2023

(54) NEEDLE HUB FOR SUBCUTANEOUS INFUSION SET

(71) Applicant: Becton, Dickinson and Company, Franklin Lakes, NJ (US)

(72) Inventor: Ralph Sonderegger, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 111 days.

(21) Appl. No.: 16/329,588

(22) PCT Filed: Sep. 14, 2017

(86) PCT No.: PCT/US2017/051611
§ 371 (c)(1),
(2) Date: Feb. 28, 2019

(87) PCT Pub. No.: WO2018/053162
PCT Pub. Date: Mar. 22, 2018

(65) Prior Publication Data
US 2019/0192771 A1    Jun. 27, 2019

Related U.S. Application Data

(60) Provisional application No. 62/395,203, filed on Sep. 15, 2016.

(51) Int. Cl.
*A61M 5/158* (2006.01)
*A61M 5/32* (2006.01)
(Continued)

(52) U.S. Cl.
CPC .......... *A61M 5/158* (2013.01); *A61M 5/162* (2013.01); *A61M 5/1626* (2013.01);
(Continued)

(58) Field of Classification Search
CPC .... A61M 5/158; A61M 5/162; A61M 5/1626; A61M 2005/1585; A61M 2005/1586;
(Continued)

(56) References Cited

U.S. PATENT DOCUMENTS 5,688,254 A    11/1997    Lopez et al.
5,968,011 A    10/1999    Larsen et al.
(Continued)

FOREIGN PATENT DOCUMENTS

JP    2004-524926 A1    8/2004
WO    WO-2013086463    6/2013

*Primary Examiner* — Kami A Bosworth
(74) *Attorney, Agent, or Firm* — Dickinson Wright PLLC (57) ABSTRACT

A needle hub (10) includes a core mounting structure (27), a first panel (28) and a second panel (29) connected to the core mounting structure (27) with an opening formed between the first panel (28) and the second panel (29), an introducer needle (72) fixedly attached to the core mounting structure (27) for insertion into a patient, and an actuation lever (16, 18) cantilevered longitudinally at a central portion thereof from the core mounting structure (27) and having an actuation button (12, 14) disposed at a proximal free end and a latch (24, 26) disposed at a distal free end.

13 Claims, 6 Drawing Sheets

(51) Int. Cl.
*A61M 5/162* (2006.01)
*A61M 25/00* (2006.01)

(52) U.S. Cl.
CPC ........ *A61M 5/3202* (2013.01); *A61M 5/3287* (2013.01); *A61M 2005/1585* (2013.01); *A61M 2025/0006* (2013.01)

(58) Field of Classification Search
CPC .............. A61M 25/0102; A61M 25/06; A61M 25/0606; A61M 25/0612; A61M 25/065
See application file for complete search history.

(56) References Cited

U.S. PATENT DOCUMENTS

| | | | |
|---|---|---|---|
| 6,293,925 B1* | 9/2001 | Safabash | A61M 5/158 604/136 |
| 2004/0158207 A1 | 8/2004 | Hunn et al. | |
| 2004/0260235 A1* | 12/2004 | Douglas | A61M 5/158 604/93.01 |
| 2006/0030815 A1 | 2/2006 | Csincsura et al. | |
| 2007/0185441 A1 | 8/2007 | Fangrow, Jr. | |
| 2009/0069750 A1* | 3/2009 | Schraga | A61M 5/14248 604/167.02 |
| 2010/0274200 A1 | 10/2010 | Nielsen | |
| 2011/0060287 A1* | 3/2011 | Ambruzs | A61M 5/158 604/164.12 |
| 2012/0029483 A1* | 2/2012 | Griffith | A61J 15/0092 604/535 |
| 2014/0155839 A1 | 6/2014 | Griffith et al. | |
| 2014/0316379 A1 | 10/2014 | Sonderegger et al. | |
| 2015/0174319 A1 | 6/2015 | Rieck | |

* cited by examiner

NEEDLE HUB FOR SUBCUTANEOUS INFUSION SET

This application claims priority under 35 U.S.C. § 119(e) from U.S. Provisional Application Ser. No. 62/395,203, filed on Sep. 15, 2016, which is incorporated herein by reference in its entirety.

FIELD OF THE INVENTION

The present invention relates generally to needle hubs, and more particularly, to introducer needle hubs for use with infusion devices, such as subcutaneous infusion devices used in conjunction with an infusion pump in the infusion of insulin and other medicaments.

BACKGROUND OF THE INVENTION

One mode of insulin infusion treatment for diabetes includes infusion pump therapy via a catheter, needle or other type of cannula. Infusion pumps offer the advantages of continuous infusion of insulin, precision dosing, and programmable delivery schedules. Together, these advantages result in more accurate blood glucose control. In this mode of insulin infusion treatment, the infusion pump remains attached to the user and required doses of insulin are delivered to the user via the pump.

One type of cannula is a catheter, which generally is a tube that can be inserted into the body to permit the administration of fluids. In infusion pump therapy, the types and sizes of the catheter may vary, but generally, the catheter is a thin, flexible tube. In some uses, however, it may be larger and/or rigid.

One type of conventional infusion set is sold as the Quick-Set® infusion set by Medtronic. In such devices, the infusion pump includes a catheter assembly connected to a pump via a tubing set, and a separate insertion device inserts and/or attaches the catheter assembly into to a user via an introducer needle provided as part of the infusion set. The infusion set and insertion device can also be combined, as in the Mio® infusion set sold by Medtronic, which is an "all-in-one" design that combines the infusion set and insertion device into one unit.

A conventional infusion device can include a fluid connector hub, which may be releasably attached to a base that can be secured to a user's skin. An infusion pump supplies fluid to a catheter via the fluid connector hub/base engagement.

With conventional infusion devices, however, there are concerns that before and during insertion of the catheter, the introducer needle and catheter may move relative to one another. There is an axial relationship between the tip of the needle and the catheter, which is commonly known as the lie distance. The lie distance is ideally maintained within a suitable range during insertion of the catheter into a user when using the tip of the needle to puncture the skin, and is also ideally maintained within a suitable range as the shank of the needle carries the catheter into the subcutaneous region.

A suitable lie distance, however, sometimes cannot be maintained because of relative movement between the introducer needle and the catheter. If the lie distance is not suitable, the piercing resistance increases and can cause significant pain for a patient.

As such, it may be appreciated that there is a continuing need for a new and improved needle hub for an introducer needle that addresses the problems noted above and is simple and low-cost to manufacture. Embodiments of the present invention substantially fulfill this need.

SUMMARY OF THE INVENTION

In accordance with an aspect of the present invention, a needle hub comprises a core mounting structure, a first panel and a second panel connected to the core mounting structure with an opening formed between the first panel and the second panel, a needle fixedly attached to the core mounting structure for insertion into a patient, and an actuation lever cantilevered at a central portion thereof from the core mounting structure and having an actuation button disposed at a proximal free end and a latch disposed at a distal free end.

In accordance with another aspect of the present invention, an insertion device comprises a needle hub including an interior cavity, a core mounting structure disposed in the interior cavity, and at least one lever pivotally connected to the core mounting structure; and an infusion set base including a column extending from the infusion set base, a head disposed at a proximal end of the post, and an undercut formed by the column and head, wherein the lever engages the undercut of the infusion set base to removably engage the needle hub with the infusion set base.

In accordance with still another aspect of the present invention, a needle hub is removably engaged with a medical device, the needle hub comprising an interior cavity and a core mounting structure disposed therein, the core mounting structure defining an introducer needle cavity in coaxial alignment with the interior cavity, the needle cavity having an introducer needle disposed therein for removably inserting into the medical device, the interior cavity having pivots connected to the core mounting structure for removably engaging actuation arms with the medical device.

BRIEF DESCRIPTION OF THE DRAWINGS

The above and/or other aspects and advantages of embodiments of the invention will be more readily appreciated from the following detailed description, taken in conjunction with the accompanying drawings, in which:

FIG. 2 is a perspective cross-sectional view.

DETAILED DESCRIPTION OF EMBODIMENTS OF THE PRESENT INVENTION

Reference will now be made in detail to embodiments of the present invention, which are illustrated in the accompanying drawings, wherein like reference numerals refer to like elements throughout. The embodiments described herein exemplify, but do not limit the present invention by referring to the drawings.

It will be understood by one skilled in the art that this disclosure is not limited in its application to the details of construction and the arrangement of components set forth in the following description or illustrated in the drawings. The embodiments herein are capable of being modified, practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

Figure 1:
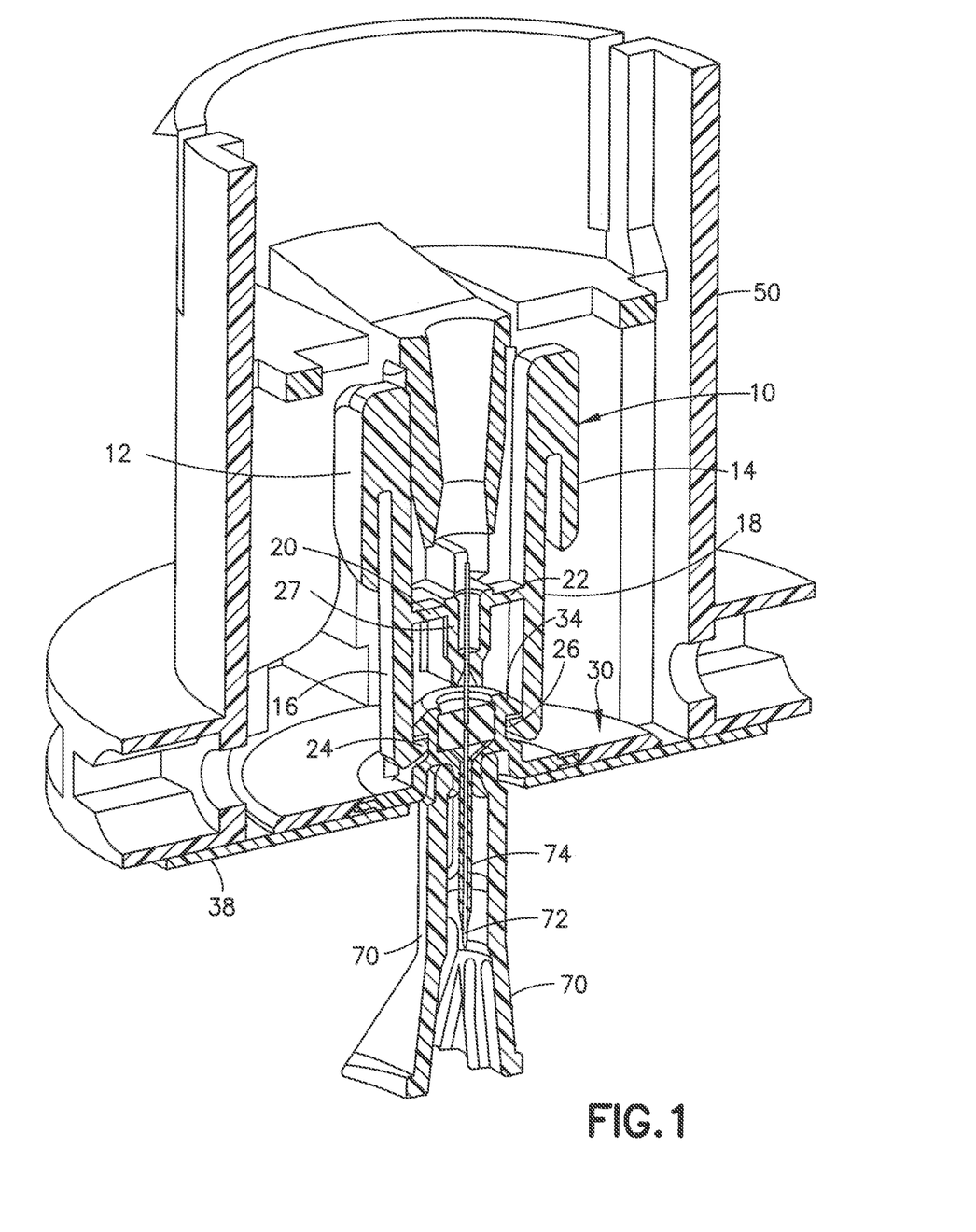
FIG. 1 is perspective a cross-sectional view of a needle hub for an insertion needle, an infusion set base and an insertion device in accordance with an embodiment of the present invention.

FIG. 1 illustrates an exemplary embodiment of a needle hub 10 of the present invention engaged with an infusion set base 30. The needle hub 10 is mounted in an insertion device 50 and a needle cover 70 protects an introducer needle 72. The infusion set base 30 is attached to an adhesive patch or pad 38 having an adhesive backing, which is used to secure the infusion set base 30 to a user's skin. Preferably, a removable adhesive liner protects the adhesive backing. FIG. 1 illustrates a state in which the needle hub 10 and infusion set base 30 are ready to facilitate insertion of a soft (flexible) catheter 74 and the introducer needle 72 into the user after removal of the needle cover 70 and the adhesive liner.

Figure 2:
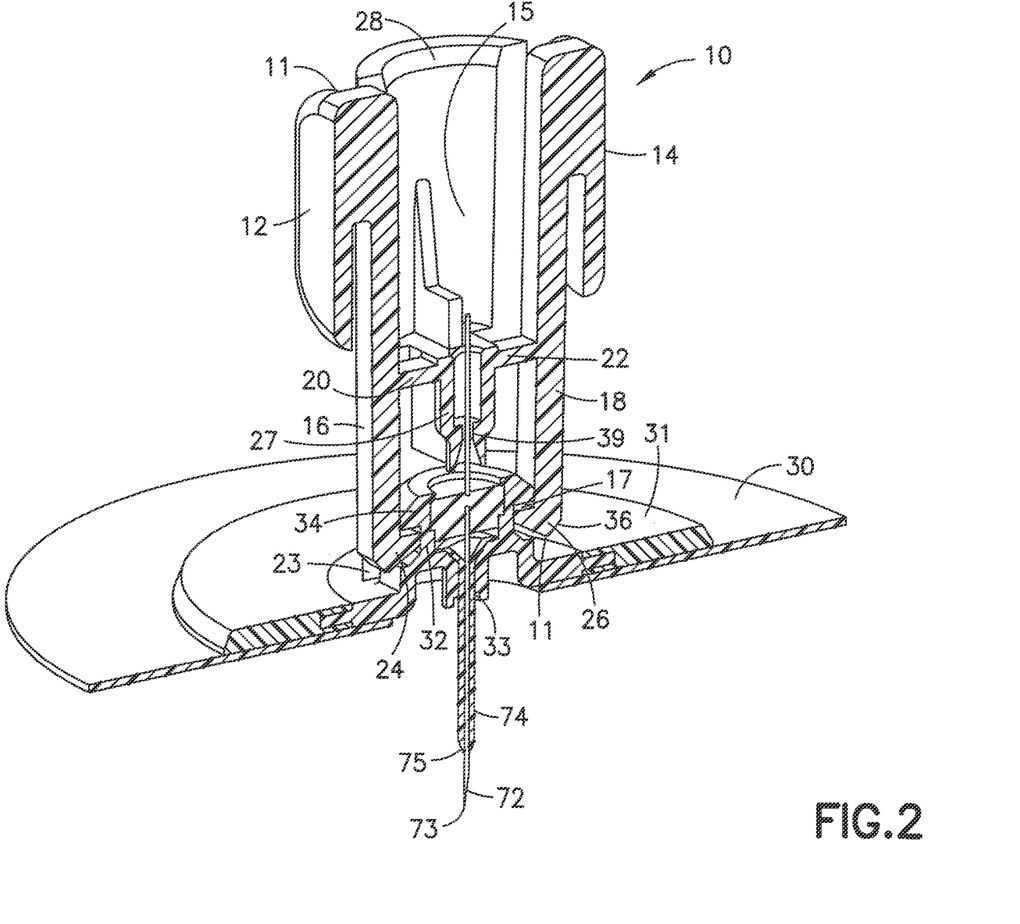
Figure 2A:
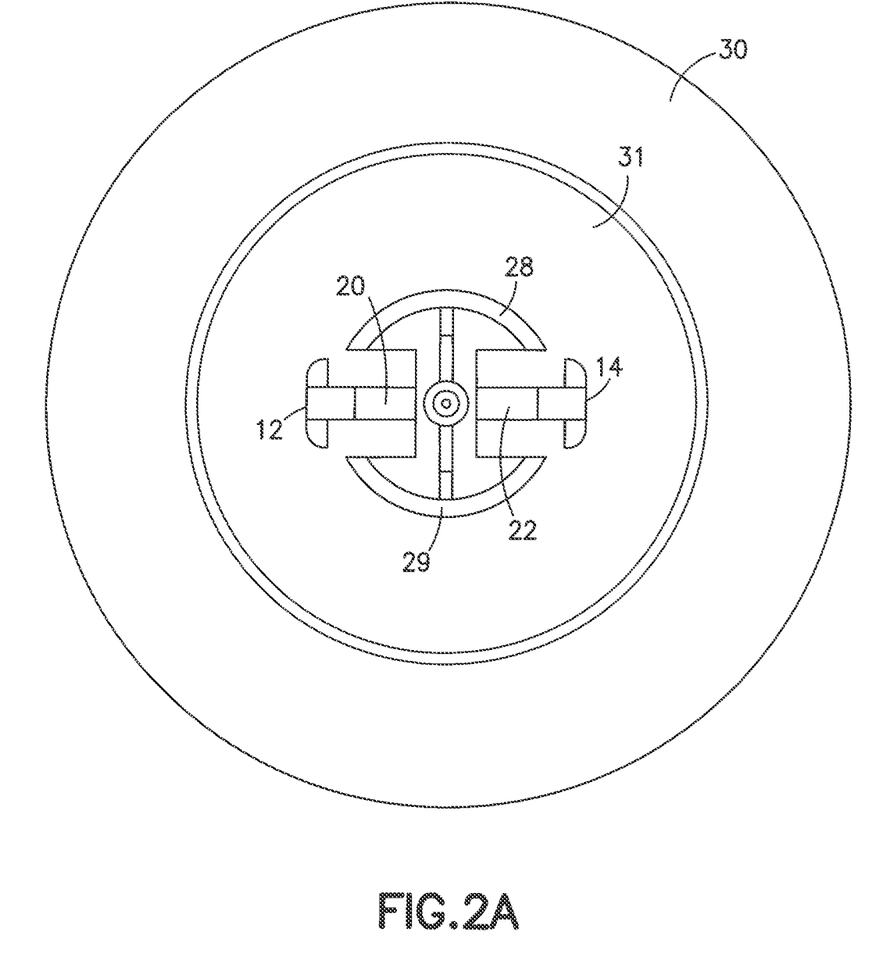
FIG. 2A is a top view, of the needle hub of FIG. 1 in a first operational state and the base of FIG. 1.

FIG. 2 is a cross-sectional view, and FIG. 2A is a top view, of the infusion set base 30 and the needle hub 10 in a first operational state. The needle hub 10 includes an interior cavity 15. In a preferred embodiment, a core mounting structure 27 includes an introducer needle cavity 39 and the introducer needle 72 is fixed to the introducer needle cavity 39 of the core mounting structure 27. The introducer needle 72 is fixed against axial movement relative to the needle hub 10. As illustrated in FIG. 2, the introducer needle cavity 39 is in coaxial alignment with the interior cavity 15. The needle hub 10 can be used to insert the introducer needle 72 and the catheter 74 into the user. The introducer needle 72 is preferably a hollow stainless steel needle with a sharp beveled tip 73.

Figure 3:
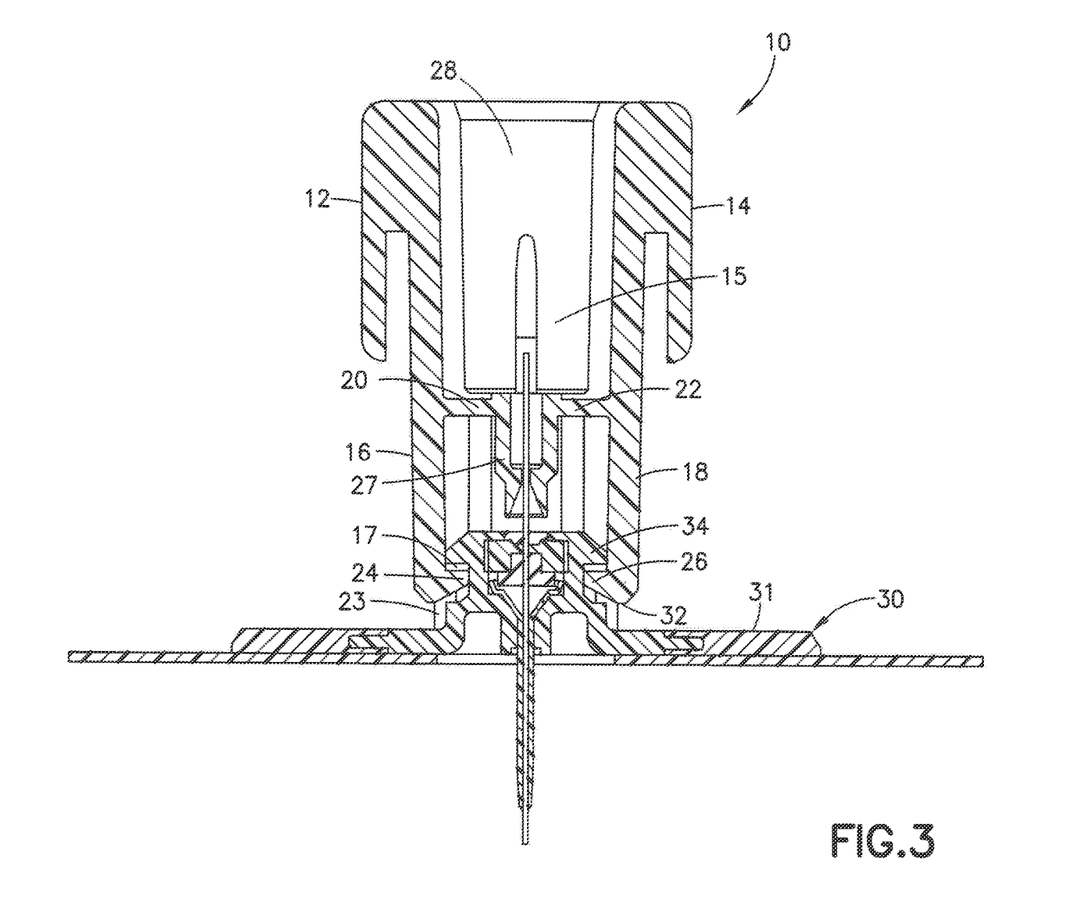
FIG. 3 is a cross-sectional view of the needle hub and the infusion set base of FIG. 1 in the first operational state.
Figure 4:
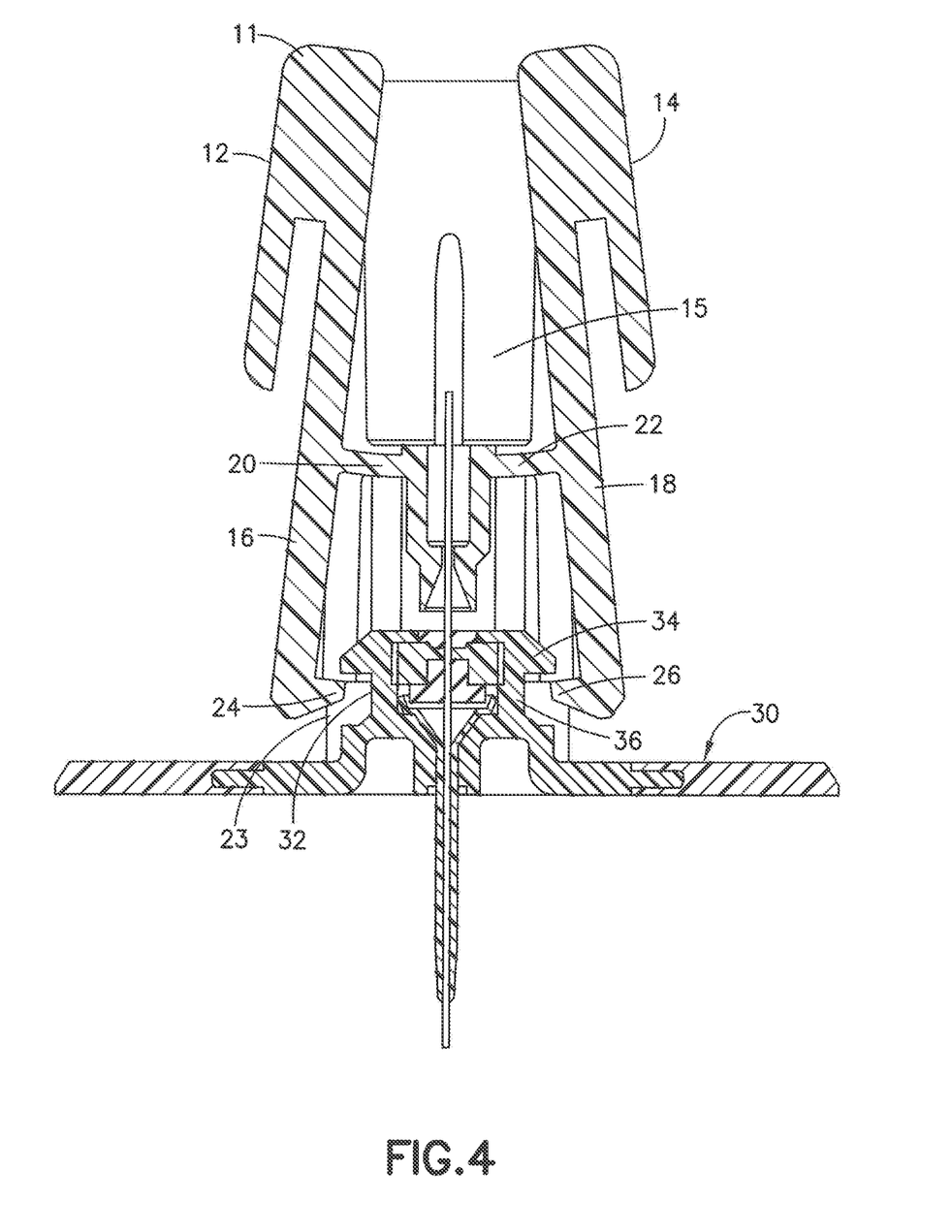
FIG. 4 is a cross-sectional view of the needle hub of FIG. 1 in a second operational state and the infusion set base of FIG. 1.

FIGS. 2-4 further illustrate features of the needle hub 10. As shown, the needle hub 10 remains engaged with the infusion set base 30 after being removed from the insertion device 50. The core mounting structure 27 located in the interior cavity 15 is connected to first and second levers 16, 18 via latch hinges 20, 22. Each lever 16, 18 includes a latch 24, 26 disposed at a distal end thereof to engage the needle hub 10 with the infusion set base 30 (see FIGS. 2 and 3). Additionally, each lever 16, 18 includes an actuation button 12, 14 disposed at a proximal end thereof. Levers 16, 18 are cantilevered longitudinally at central portions thereof from the core mounting structure 27. A first panel 28 and a second panel 29 (the latter shown in FIG. 2A) of the needle hub 10 are also connected to the core mounting structure 27. As shown in FIGS. 2 and 3, a distal end 23 of the first panel 28 extends further distally than first and second latches 24, 26 to engage an upper surface 31 of the infusion set base 30. This engagement promotes stability. Preferably, the distal end of the second panel 29 extends similarly.

Features of the needle hub 10 in a first state (prior to a user depressing the first and second actuation buttons 12, 14 and removing the needle hub 10 from the infusion set base 30) are illustrated in FIGS. 2 and 3. As shown, the infusion set base 30 includes a columnar post 32 surrounding an internal cavity 33. A head 34 is disposed at a proximal end of the post 32. The head 34 may be configured in a mushroom-shape. According to one embodiment, the catheter 74 is fixedly connected to the internal cavity 33 of the columnar post 32. The introducer needle 72 can be removably disposed within the catheter 74 with the lie distance (distance between the catheter tip 75 and the needle tip 73) maintained by the needle hub 10 engaging the infusion set base 30.

As previously stated, the actuation buttons 12, 14 include levers 16, 18 connected to the core mounting structure 27 via latch hinges 20, 22. Each of the levers 16, 18 includes a latch 24, 26 disposed at a distal end thereof and can removably engage the undercut 36 formed by column 32 and head 34 on the infusion set base 30. When the actuation buttons 12, 14 are in a first, non-actuated state, the latches 24, 26 engage with the undercut 36 of the infusion set base 80 and the distal ends of the first and second panels 28, 29 sit on the upper surface 31 of the infusion set base 30 (see FIG. 3). As shown, the head 34 extends into a distal opening 17 of the needle hub 10.

FIG. 4 illustrates the needle hub 10 in a second state, in which the user depresses the actuation buttons 12, 14. Preferably, the actuation buttons 12, 14 flex inward at a proximal end 11 of the needle hub 10 through openings between the first and second panels 28, 29 when a user depresses the actuation buttons 12, 14. The levers 16, 18 pivot at latch hinges 20, 22 causing the latches 24, 26 to flex radially outward away from the undercut 36 on the infusion set base 30. As shown in FIG. 4, when the actuation buttons 12, 14 are in the second state and the latches 24, 26 are disengaged from the undercut 36 of the infusion set base 30, the first and second panels 28, 29 remain disposed on an upper surface 31 of the infusion set base 30.

Figure 5:
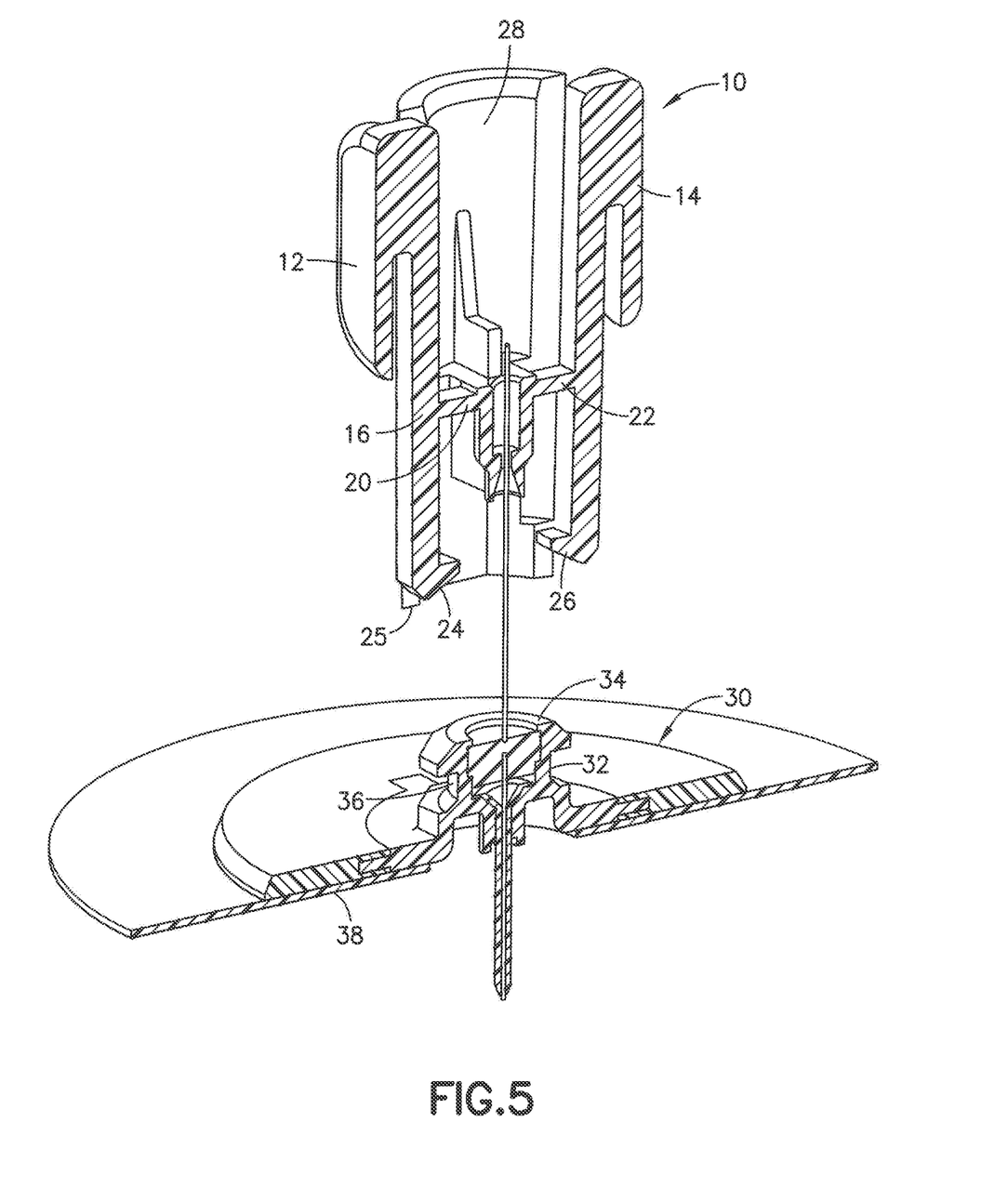
FIG. 5 is a cross-sectional view of the needle hub of FIG. 1 in a fully deployed state and removed from the infusion set base of FIG. 1.

FIG. 5 illustrates a state in which the needle hub 10 is in the process of being removed from the infusion set base 30, and the first and second panels 28, 29 are removed from the upper surface 31 of the infusion set base 30. The user maintains pressure on the actuation buttons 12, 14 while lifting the needle hub 10 relative to the infusion set base 30, at least until latches 24, 26 clear the head 34. After the needle hub 10 is removed and the user releases pressure on the actuation buttons 12, 14, the latch hinges 20, 22 also release and the latches 24, 26 return to the unflexed position of the first state. As shown in FIG. 5, the user can now complete withdrawal of the introducer needle 72 from the catheter 74 of the infusion set base 30.

Although no needle stick prevention mechanism is shown, some embodiments of the present invention include a needle stick prevention mechanism. The ability to protect users and medical personnel from needle stick injury is a safety aspect in the field of infusion set devices.

Referring back to FIG. 1, in one embodiment, the needle hub 10 includes a needle cover 70 where the needle cover 70 engages with the infusion set base 30 in an initial state. According to one embodiment, when the needle hub 10 is removed from the infusion set base 30, the needle cover 70 can cover the introducer needle 72 mounted to the need hub 10 to prevent a needle stick injury. For example, the latches 24, 26 could engage the needle cover 70 to retain the needle cover 70 on the needle hub 10, e.g., via recesses in the needle cover's exterior. Alternatively, or in addition, the distal end of the core mounting structure 27 can be configured to mate with the proximal end of the needle cover 70, similar to the way the proximal end of the needle cover 70 mates with the infusion set base 30.

According to another embodiment, a separate needle tip shield can cover the needle tip and engage the needle hub 10 once the needle hub 10 is removed from the infusion set base 30.

It will be appreciated by those skilled in the art that changes may be made to the embodiment described herein without departing from the scope of the invention. It is particularly noted that the features of different embodiments and claims may be combined with each other as long as they do not contradict each other. All such changes and combinations are considered to be within the scope of the invention, which is defined by the appended claims and their equivalents.

The invention claimed is:

1. A needle hub comprising:
a core mounting structure;
a first panel and a second panel connected to the core mounting structure with an opening formed between the first panel and the second panel;
a needle fixedly attached to the core mounting structure and extending distally further than the first and second panels for insertion into a patient; and
an actuation lever disposed within the opening, cantilevered at a central portion of the actuation lever from the core mounting structure, and having an actuation button disposed at a proximal free end and a latch disposed at a distal free end;
wherein the first panel and the second panel extend further distally than the latch of the actuation lever and are configured to promote stability of the needle hub during attachment of the latch to a medical device.

2. The needle hub as recited in claim 1, further comprising a second actuation lever cantilevered at a central portion thereof from the core mounting structure and having an actuation button disposed at a proximal free end and a latch disposed at a distal free end, wherein the first actuation lever and the second actuation lever are configured to releasably couple the needle hub to the medical device.

3. The needle hub as recited in claim 2, wherein distal ends of the first and second panels are configured to engage an upper surface of the medical device.

4. An insertion device comprising:
a needle hub according to claim 1; and
an infusion set base including:
a base portion;
a central post extending from the base portion of the infusion set base;
a head disposed at a proximal end of the post; and
an undercut formed by the post and the head, wherein the actuation lever engages the undercut of the infusion set base to removably engage the needle hub with the infusion set base;
wherein when the needle hub is assembled with the infusion set base, the first panel and the second panel engage the base portion.

5. The insertion device as recited in claim 4, wherein the latch is configured to removably engage the undercut of the infusion set base.

6. The insertion device as recited in claim 4, further comprising a second actuation lever pivotally connected to the core mounting structure.

7. The insertion device as recited in claim 6, further comprising a latch disposed at a distal free end of the second actuation lever for removably engaging the undercut of the infusion set base.

8. The insertion device as recited in claim 4, at least a portion of the needle is disposed in a needle cavity defined by the core mounting structure for inserting into a patient's skin.

9. The insertion device as recited in claim 4, further comprising a cannula depending distally from the base portion, wherein when the needle hub is assembled with the infusion set base, the needle extends distally beyond a distal end of the cannula.

10. The insertion device as recited in claim 9, wherein the needle is sharpened and extends through the cannula for insertion of the needle and the cannula into a patient.

11. The insertion device as recited in claim 9, wherein the needle is coaxial with the cannula.

12. The needle hub as recited in claim 1, wherein the needle is sharpened.

13. The needle hub as recited in claim 12, wherein the needle hub is configured for coaxial insertion of the needle and a cannula of the medical device into a patient.

* * * * *

UNITED STATES PATENT AND TRADEMARK OFFICE
CERTIFICATE OF CORRECTION

| | | |
|---|---|---|
| PATENT NO. | : 11,547,795 B2 | Page 1 of 1 |
| APPLICATION NO. | : 16/329588 | |
| DATED | : January 10, 2023 | |
| INVENTOR(S) | : Ralph Sonderegger | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 118 days.

Signed and Sealed this
First Day of July, 2025

Coke Morgan Stewart
*Acting Director of the United States Patent and Trademark Office*